United States Patent [19]

Komatsu et al.

[11] 4,268,690

[45] May 19, 1981

[54] PROCESS FOR PRODUCING TEREPHTHALIC ACID OF HIGH PURITY

[75] Inventors: Makoto Komatsu; Tazuo Ohta; Toru Tanaka; Ryoichi Oda; Yuji Takamizawa, all of Kurashiki, Japan

[73] Assignee: Mitsubishi Gas Chemical Company, Inc., Tokyo, Japan

[21] Appl. No.: 55,198

[22] Filed: Jul. 2, 1979

[30] Foreign Application Priority Data

Jul. 21, 1978 [JP] Japan ................... 53-88992

[51] Int. Cl.$^3$ ....................... C07C 51/16; C07C 51/42
[52] U.S. Cl. .................... 562/416; 562/486; 562/487
[58] Field of Search ........................ 562/416, 486, 487

[56] References Cited

U.S. PATENT DOCUMENTS 2,838,565  6/1958  Heath et al. ........................ 562/486
3,522,298  7/1970  Bryant et al. ....................... 562/487
3,678,106  7/1972  Ager ................................... 562/416

Primary Examiner—Alan Siegel
Attorney, Agent, or Firm—Armstrong, Nikaido, Marmelstein & Kubovcik

[57] ABSTRACT

Terephthalic acid of high purity is continuously produced in a high yield by oxidizing p-tolualdehyde with a molecular oxygen-containing gas in the presence of bromine ions as a catalyst in a water solvent, contacting the resulting slurry solution containing crude terephthalic acid with an ascending stream of high temperature water of 180°–320° C., and withdrawing the water solvent together with the ascending stream of high temperature of water upwardly, while settling down crystalline terephthalic acid through the ascending stream of high temperature water and withdrawing the crystalline terephthalic acid together with a portion of the high temperature water downwardly.

12 Claims, No Drawings

PROCESS FOR PRODUCING TEREPHTHALIC ACID OF HIGH PURITY

This invention relates to a process for producing terephthalic acid of high purity by oxidizing p-tolualdehyde with a molecular oxygen-containing gas in the presence of bromine ions in a water solvent, and bringing the resulting slurry solution containing crude terephthalic acid in contact with high temperature water.

It is disclosed in Japanese Patent Publication No. 13921/64 (British Pat. No. 833,438) or Japanese Laid-open patent application No. 4019/71 (USP No. 3678106) to oxidize an aromatic compound having an alkyl substituent or a partially oxidized alkyl substituent in the presence of bromine ions in a water solvent, but these prior arts have no disclosure of specific examples of oxidation of p-tolualdehyde, and thus no knowledge of optimum process conditions can be obtained therefrom. Furthermore, the disclosed examples are all directed to small-scale batch tests and fail to provide any industrially applicable continuous process. Still furthermore, the terephthalic acid thus obtained contains a large amount of impurities such as 4-CBA (4-carboxybenzaldehyde), etc. and cannot be used, as it is, as a raw material for polyester fibers.

The present invention provides a continuous process for producing terephthalic acid of high purity in a high yield in an industrially operable manner from p-tolualdehyde as a raw material, the p-tolualdehyde being recently obtainable from toluene and carbon monoxide in an industrial scale.

According to the present invention, p-tolualdehyde is oxidized with a molecular oxygen-containing gas in the presence of bromine ions in a water solvent, and the resulting slurry solution containing crude terephthalic acid is led into an ascending stream of high temperature water at 180°–310° C., where the water solvent ascends together with the ascending stream of high temperature water, whereas crystalline terephthalic acid settles down through the high temperature water and is withdrawn downwardly together with a portion of the high temperature water.

Any catalyst can be used in the oxidation reaction of p-tolualdehyde in the present invention, so long as it is a material capable of generating bromine ions under reaction conditions, such as hydrogen bromide, ethyl bromide, sodium bromide plus hydrogen chloride, etc. When a compound of heavy metal such as manganese, cerium, etc. is used together, terephthalic acid of much higher purity can be obtained.

The amount of bromine ions to be added is 0.5–12% by weight, preferably 0.5–6% by weight, and more preferably 1–4% by weight, on the basis of the solvent. If the amount of bromine ions is less than 0.5% by weight on the basis of the solvent, combustion and decomposition of p-tolualdehyde are remarkable, and at the same time the resulting terephthalic acid has very much increased contents of 4-carboxybenzaldehyde or coloring impurities. Above 12% by weight, on the other hand, the reaction is suppressed.

Reaction temperature is 180°–280° C., preferably 210°–260° C.

Reaction pressure is generally automatically determined in a process of keeping the temperature constant by evaporation, condensation and refluxing of the water solvent, but can be maintained at a desired constant value by an outside heat exchange means. The reaction pressure range is not particularly restricted, so long as it can keep the reaction solution in a liquid phase, but usually a reaction pressure range of 10–70 kg/cm$^2$ gage is utilized.

Either oxygen or air can be utilized as an oxidizing agent, but it is economically more advantageous to utilize the air.

The amount of water to be used as the solvent is at least two times the weight of raw material p-tolualdehyde, preferably 3–6 times the weight of the latter.

The reaction can be carried out batchwise, semi-continuously or continuously, but the continuous reaction is preferable from the industrial viewpoint.

The resulting reaction product solution is in a form of slurry containing the raw material p-tolualdehyde, p-toluic acid, 4-CBA, catalyst and other impurities in addition to terephthalic acid, and a reaction mother liquor containing these impurities exists among crystalline particles of the product terephthalic acid. The reaction mother liquor existing among these crystalline particles cannot be separated from the particles even by centrifuge or other mechanical means, and a complicated purification step is required for obtaining terephthalic acid of fiber grade.

In the present invention, the slurry solution of terephthalic acid containing the impure mother liquor is brought in contact with high temperature water of 180°–310° C., whereby crystalline particles of crude terephthalic acid are suspended in the high temperature water and made to settle down through the high temperature water, and the purity of crystalline particles of terephthalic acid can be considerably improved thereby. The present invention is based on that finding.

It is necessary in the present invention to separate the slurry solution of crude terephthalic acid as the reaction product into crystalline particles of terephthalic acid and the reaction solvent in the high temperature water, and this can be satisfactorily attained by a means of leading the slurry solution into an ascending stream of high temperature water introduced at a bottom of a column.

Temperature of the high temperature water is 180°–310° C., and if the temperature is lower than 180° C., the reaction impurities cannot be completely dissolved in the high temperature water, but are deposited and settle down to lower the purity of terephthalic acid.

Too high a temperature gives no particular disadvantage, but the pressure is increased. Thus, a temperature higher than necessary is not economical.

The pressure is high enough to keep the high temperature water in said temperature range, and is almost automatically determined, if the temperature is given.

Flow velocity of the ascending stream of the high temperature water depends also upon the structure of apparatus, size of crystalline particles, etc., but is preferably about 0.001—about 0.01 m/sec.

If the flow velocity is too low, separation of the crystalline particles from the reaction solvent is unsatisfactory, and the purity of terephthalic acid is thus lowered. If it is too high on the other hand, a portion of crystalline particles of terephthalic acid does not satisfactorily settle down and is withdrawn upwardly together with the ascending stream.

A desirable structure of an apparatus for separating the crystalline particles from the reaction solvent is a column-type, so that the ascending stream of the high temperature water can flow upwards with some linear velocity without any back-mixing. For that purpose, a column with appropriate baffles inside or a column with perforated trays can be preferably used. A stirrer is not always necessary within the column, but is effective for assuring a good contact of the crystalline particles with the high temperature water and removing the accompanying reaction mother liquor from the crystalline particles, while the crystalline particles are suspended in the high temperature water and settle down therethrough. For that purpose, use of the so-called RDC (rotary disc contactor) is particularly preferable.

A liquid stream from the column top of the apparatus consists essentially of water, and contains some terephthalic acid, catalyst, reaction impurities, etc., and can be reused as the reaction solvent as it is, or after appropriate concentration.

A liquid stream from the column bottom is a slurry solution of purified terephthalic acid crystal in the high temperature water, and can be cooled, crystallized and centrifuged, as it is, but can be, if necessary, heated to dissolve the crystal, hydrogenated in the presence of a catalyst of platinum group metal, cooled, crystallized and separated. In the latter case, the hydrogenation can be generally carried out at a hydrogenation temperature of 200°–330° C. and a pressure of 16–100 kg/cm$^2$ gage for a contact time of 0.005–10 hours.

In the present invention, the purity of terephthalic acid crystal can be considerably improved by such a simple means as to lead a slurry solution resulting from the oxidation of p-tolualdehyde in the water solvent into the ascending stream of high temperature water, as described above, and particularly a problem of corrosion of apparatuses due to the bromine ions used as the catalyst can be effectively and completely solved after the hydrogenation or crystallization step, and terephthalic acid can be continuously produced in a high yield with a high purity.

EXAMPLE

Oxidation reaction is carried out in a zirconium oxidation reactor having a net volume of 30 l, provided with a reflux cooler, a stirrer, a heater, a feed inlet, a gas inlet, and a product outlet. Connected to the product outlet of the reactor is a zirconium cylindrical separator column (inside diameter: 25 mm, effective height: 1,500 mm) provided with a heater, a reaction product inlet connecting to the oxidation reactor, a hot water inlet, an upper outlet and a lower outlet. The reaction product inlet is positioned at a level of 750 mm from the bottom of the separator column, and the hot water inlet at a level of 200 mm from the bottom. Receptacles having a net volume of 50 l are connected to the upper outlet and the lower outlet, respectively, of the separator column. The receptacle each is provided with a reflux cooler, a stirrer, and a liquid level detector.

Before the oxidation reaction, the separator column is heated to keep a temperature of 250° C., and hot water of 250° C. is supplied thereto at the hot water inlet at a rate of 5.7 kg/hr, and after the separator column is filled with the hot water, the hot water is allowed to be discharged into the receptacles at the upper and lower parts.

Into the oxidation reactor are charged 10 kg of water, 158 g of hydrogen bromide, and 282 g of manganese bromide in advance. Nitrogen is supplied under pressure to the oxidation reactor at the gas inlet to increase the pressure of the oxygen reactor to 10 kg/cm$^2$ gage, and then the oxidation reactor is heated to 245° C. by the heater. When the temperature reaches 245° C., air is introduced into the oxidation reactor at the gas inlet, and at the same time 1.8 kg/hr of p-tolualdehyde and 5.5 kg/hr of the aqueous solution of manganese bromide-hydrogen bromide having the same composition as initially charged are continuously charged into the oxidation reactor, and a liquid level of the oxidation reactor is kept constant.

When the oxidation reaction reaches a stationary state, a product slurry solution is led to the separator column at a rate of 7.1 kg/hr, and 6.2 kg/hr of the liquid stream (containing 0.6 kg/hr of terephthalic acid) is withdrawn from the separator column at the column top, and 6.6 kg/hr of the liquid stream (containing 1.8 kg/hr of terephthalic acid) is withdrawn at the column bottom.

Terephthalic acid crystal is separated from the liquid stream withdrawn at the column bottom, and washed with hot water to obtain product terephthalic acid.

Properties of terephthalic acid obtained at the stationary state are as follows:

4CBA content—265 ppm

OD$_{340}$—0.091

OD$_{340}$ is a light absorbancy at 340 m$\mu$ obtained by dissolving 2 g of terephthalic acid in 25 ml of 2NKOH and measuring it in a 50 mm long cell, and reflects the content of colored impurities or coloring materials in terephthalic acid. The lower the OD$_{340}$ value, the less the colored impurities.

Comparative Example 1

Operations are carried out in the same manner as in Example except that the operating temperature of the separator column is 150° C., that is, the temperature of hot water supplied to the separator column is 150° C.

Properties of the resulting terephthalic acid are as follows:

4CBA content—450 ppm

OD$_{340}$—0.41

Comparative Example 2

Operations are carried out in the same manner as in Example except that the reaction product is directly led to the receptacle from the oxidation reactor without passing it through the separator column.

Properties of the resulting terephthalic acid are as follows

4CBA content—591 ppm

OD$_{340}$—0.59

Polyethylene terephthalate obtained by direct polycondensation of the terephthalic acid produced in Example with ethylene glycol according to the ordinary process has colorless, but those obtained from the terephthalic acid of Comparative Examples 1 and 2 are yellow.

What is claimed is:

1. A process for producing terephthalic acid of high purity, which comprises oxidizing p-tolualdehyde as a raw material with a molecular oxygen-containing gas in the presence of bromine ions as a catalyst in a water solvent, introducing the resulting slurry solution containing crude terephthalic acid into an ascending liquid stream of high temperature water of 180°–310° C. having a flow velocity of 0.0001–0.01 m/sec, and withdrawing the water solvent together with the ascending stream of high temperature water upwardly, while allowing crystalline terephthalic acid to settle down through the ascending stream of high temperature water and withdrawing the crystalline terephthalic acid together with a portion of the high temperature water downwardly.

2. A process according to claim 1, wherein the slurry solution is contacted with the ascending stream of high temperature water in a column-type separator.

3. A process according to claim 2, wherein the column-type separator is a rotary disc contactor.

4. A process according to claim 1, wherein the crystalline terephthalic acid downwardly withdrawn together with a portion of the high temperature water is further heated, thereby dissolving the terephthalic acid, and hydrogenated in the presence of a catalyst of platinum group metal.

5. A process according to claim 4, wherein the hydrogenation is carried out at 200°–330° C. and 16–100 kg/cm$^2$ gage for a contact time of 0.005–10 hours.

6. A process according to claim 1, wherein 0.5–12% by weight of the bromine ions is present on the basis of the water solvent.

7. A process according to claim 1, wherein the catalyst is hydrogen bromide, ethyl bromide or sodium bromide plus hydrogen chloride.

8. A process according to claim 1, wherein the oxidation is carried out in the further presence of a compound of manganese or cerium.

9. A process according to claim 1, wherein the oxidation is carried out at 180°–280° C. and 10–70 kg/cm$^2$ gage.

10. A process according to claim 1, wherein the molecular oxygen-containing gas is air.

11. A process according to claim 1, wherein the water solvent is used in a weight at least two times that of p-tolualdehyde.

12. A process according to claim 11, wherein the water solvent is used in a weight 3–6 times that of p-tolualdehyde.

* * * * *